United States Patent
Iwasaki

(10) Patent No.: US 6,927,272 B2
(45) Date of Patent: Aug. 9, 2005

(54) ELECTRONIC COMPONENT-USE MATERIAL AND ELECTRONIC COMPONENT USING IT

(75) Inventor: Kazumi Iwasaki, Nara (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 22 days.

(21) Appl. No.: 10/333,772

(22) PCT Filed: May 31, 2002

(86) PCT No.: PCT/JP02/05397
§ 371 (c)(1),
(2), (4) Date: May 19, 2003

(87) PCT Pub. No.: WO02/100138
PCT Pub. Date: Dec. 12, 2002

(65) Prior Publication Data
US 2004/0091511 A1 May 13, 2004

(30) Foreign Application Priority Data
Jun. 1, 2001 (JP) .................................. 2001-166617

(51) Int. Cl.[7] ...................... C08G 59/68; A01N 25/34
(52) U.S. Cl. ...................... 528/88; 424/405; 428/901
(58) Field of Search ..................... 424/405; 528/88; 428/901, 209

(56) References Cited

U.S. PATENT DOCUMENTS 6,387,387 B1 * 5/2002 Haniu et al. ................ 424/409
6,403,894 B1 * 6/2002 Iwasaki et al. ............. 174/256
6,475,328 B2 * 11/2002 Haniu et al. ............. 156/307.3
6,477,038 B2 * 11/2002 Iwasaki et al. ............. 361/679

FOREIGN PATENT DOCUMENTS

| EP | 0 771 526 | 5/1997 |
| EP | 0 856 556 | 8/1998 |
| JP | 10-212207 | 8/1998 |
| JP | 2001-48706 | 2/2001 |

OTHER PUBLICATIONS

Japanese Search Report for Application No. PCT/JP02/05397 dated Sep. 17, 2002.

English translation of PCT/ISA/210.

* cited by examiner

*Primary Examiner*—Cathy F. Lam
(74) *Attorney, Agent, or Firm*—RatnerPrestia

(57) ABSTRACT

Material of electronics component and electronics components using the same material are provided. The material includes repellent that can withstand severe solder-mounting conditions, and the electronics components such as printed wiring boards can lasts repelling effect for a long period. The material is used in electronics components requiring a soldering process, and includes at least curable resin, filler and the repellent. The repellent has vapor pressure of less than 10,000 nPa at room temperature. Film is formed using the material at a given place of an electronics component such as a printed wiring board.

15 Claims, 7 Drawing Sheets

ELECTRONIC COMPONENT-USE MATERIAL AND ELECTRONIC COMPONENT USING IT

THIS APPLICATION IS A U.S. NATIONAL PHASE APPLICATION OF PCT INTERNATIONAL APPLICATION PCT/JP02/05397 filed May 31, 2002.

TECHNICAL FIELD

The present invention relates to electronics-component material that includes repellents effective in repelling vermin (cockroach, ant, spider, and the like) or preventing the vermin from building nests in home-use or business-use electronics apparatuses that are possibly damaged reliability (halt, malfunction, and the like) by the vermin. The present invention also relates to electronics components using the same material.

BACKGROUND ART

Manufacturers have not anticipated that vermin invade an electronics apparatus and lower the reliability. Thus no positive countermeasure have been taken against the vermin, and such environment results in publicizing no information about failures, troubles or abrupt malfunctions of electronics apparatuses due to carcasses or droppings of the vermin. As a result, only a few ideas have been adopted in the countermeasure against the vermin, such as, a housing shape of an electronics apparatus is changed, molding material or paint including repellent is placed or painted on an invading route. However, those measures are not compatible with downsize of the electronics apparatuses, and applying the paint including the repellent to stuffed printed wiring boards possibly incurs lowering the insulation of the electronics circuits. Therefore those measures have not prevailed in the industry.

A technique of mixing repellent directly to ink material such as solder-resist was introduced as a method of producing material, which included the repellent, of electronics components. The printed wiring board, employing this conventional material that includes the repellent, cannot maintain the vermin repelling effect for a long period because an amount of the repellent decreases substantially (vaporization, decomposition, polymerization) due to heating for soldering parts to mount. To overcome this inconvenience, an amount of the repellent corresponding to the amount decreased should be mixed additionally. The greater amount of repellent lowers film-forming property (printability, hardness of film surface, adherence), increases the cost, and does not suit enough to parts-mounting by flow-soldering, namely, solder-flow mounting process (applied mainly to single-sided printed wiring board).

Heating and radiating ultraviolet, in particular, during the production of the printed wiring board tend to vaporize, decompose and polymerize the repellent, and result in shortening a repellant effective period.

To overcome those inconveniences, Japanese Patent Application No. H09-018117 discloses a technique of mixing repellent directly into material of electronics components.

In this material, repellent having a heat decomposition temperature of 250 degrees is used, so that the material withstands the solder-flow mounting process (applied mainly to single-sided printed wiring board) and achieves an initial repelling rate of approx. 95%.

Recently, the market has demanded higher reliability against vermin of various apparatuses such as home-use and business-use telephones, security system, alarm, POS system, intercom with camera, vending machine, portable telephone and PHS base station, public telephone, card reader. As a matter of course, a printed wiring board (PWB) with copper through-holes and a multi-layer PWB mainly used in those apparatuses have been strongly required to employ the material including the repellent.

However, parts-mounting to the foregoing boards uses solder-paste in soldering, i.e., solder-reflow mounting process, so that it takes as long as 30–180 seconds to raise the board surface temperature of 200° C. to the peak temperature of, e.g., 240° C. Thus the repellent in the conventional material decreases (vaporization, decomposition, polymerization) and cannot fully exert its repelling effect (initial repelling rate: approx. 30%). Further, it is very rare that a PWB with copper through-holes or a multi-layer PWB with copper through-holes completes its parts-mounting through only a single solder-reflow process.

To be more specific, on those boards, parts with lead-wires and surface-mounted parts intermingle with each other, so that parts are mounted by solder-reflow and solder-flow, or solder-reflow and again solder-reflow. As such, various combinations of solder-reflow and solder-flow are used in the parts-mounting process. The PWBs and other electronics components undergo severe heating condition throughout the foregoing mounting process, so that substantial amount of the repellent in the conventional board decreases and the repelling effect also decreases (initial repelling rate: 10%).

Therefore, the material cannot be used in the PWB that needs the foregoing mounting process. On top of that, lead-free solder has been widely used to meet the environmental protection movements. In the case of using the lead-free solder in part-mounting, a proper peak temperature of a board ranges 260–280° C. at solder-flow mounting, and 250–270° C. at solder-reflow mounting.

The higher peak temperature needs to set a retention time of the board (raise the board surface temperature of 200° C. to the peak temperature of e.g., 260° C.) 60–240 seconds. Under those severe heating condition, the conventional material including the repellent or the PWB using the material incurs substantial decrease (vaporization, decomposition, polymerization) of the repellent, and the repelling effect completely disappears (initial repelling rate: 0%). As a result, the conventional material including the repellent cannot be used in the parts-mounting that employs lead-free solder.

DISCLOSURE OF THE INVENTION

The present invention provides electronics-component material including repellent of which vapor pressure is less than 10,000 nPa at room temperature, and electronics components using the same material.

DETAILED DESCRIPTION OF THE PREFERRED EMBODIMENTS OF THE INVENTION

Figure 1:
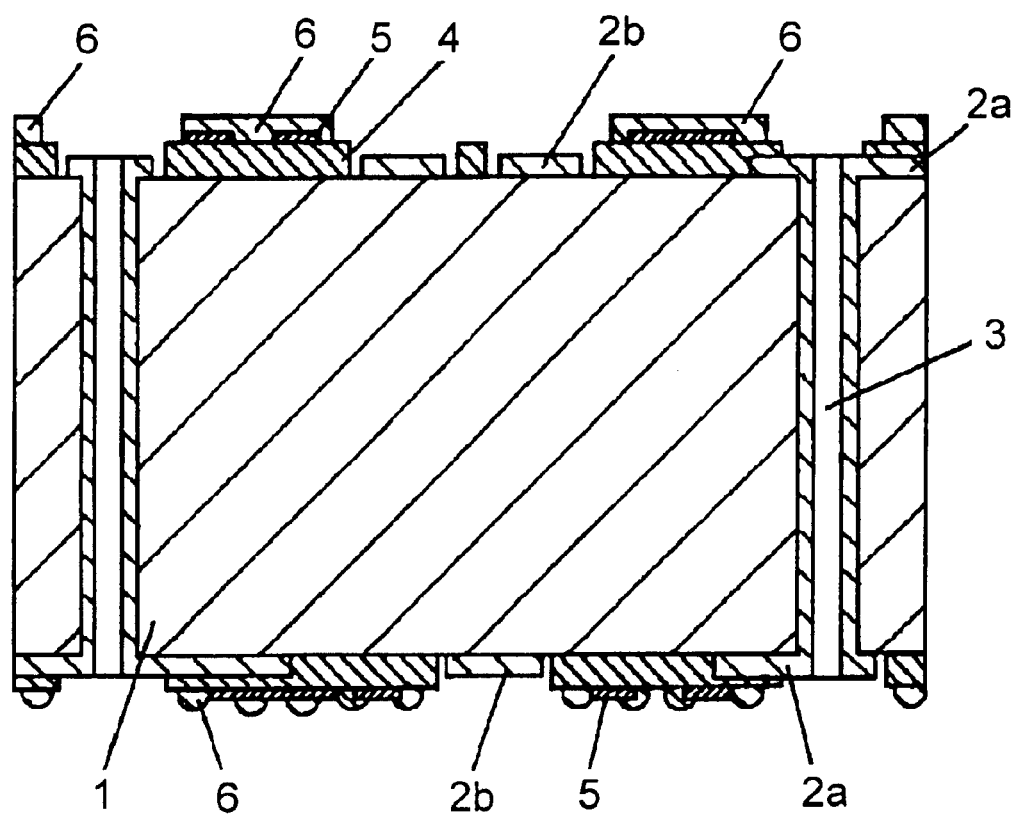
FIG. 1 is a sectional view of a printed wiring board (PWB) in accordance with a first exemplary embodiment of the present invention.

A printed wiring board (PWB), in general, is mounted with components such as semiconductors, resistors and the like and accommodated in a housing of an electronics apparatus. During an operation of the electronics circuit, the PWB is fed with power and generates heat, electromagnetic wave, or ozone. When the PWB becomes warm at 20–35° C. due to generating heat, the warm environment invites cockroaches to build nests on the PWB surface, under the PWB or around the PWB, because the growth rate of the cockroach is subject to ambient temperature. As a result, failures of continuity or insulation due to droppings or carcasses are reported. The ants are influenced by electromagnetic wave or ozone, and build a nest on a PWB surface near to the source of electromagnetic wave or ozone. They bite off components around them with their sharp teeth or corrode the nearby components with their secretion (formic acid).

The PWB as an electronics component of the present invention is furnished with vermin repelling effect, and the effect can last after the PWB is mounted with semiconductors and resistors by soldering. This point is a difference from the conventional vermin-repelling measures that is provided to PWBs after components are soldered or to housings of apparatuses.

Vermin, such as cockroaches or ants that have sensory nerve, are equipped with cuticule structure at their legs' surface or tactile sense. The vermin probe a PWB with the tactile sense or the legs having the foregoing structure when they invade the PWB. A sheet of film including the repellent is placed on the PWB of the present invention at the surface or invading routes.

The repellent included in electronics-component of the present invention employs pyrethroid-base or pyrethroid-like neurotransmitting agents that stimulate only vermin such as cockroaches or ants having sensory nerve because those agents take advantage of difference in skin structure between human being and vermin. The agents are thus not harmful to human being.

The electronics-component material and electronics components of the present invention do not intend to kill the vermin, but repeat to give the vermin learning effect, and make the vermin be repelled again and again so that the vermin will not build a nest in the electronics apparatus.

The electronics-component material of the present invention is used in electronics components including PWBs that need soldering. Therefore, the material can withstand the condition of the manufacturing process and high temperatures in the combination of solder-flow mounting and solder-reflow mounting, and its repellent effect can last for a long period.

At least one of the ingredients such as repellent, curable resin, filler and the like, which form electronics-component material is eligible to suit the physical, mechanical or heat-resisting properties. The electronics component is manufactured using this eligible ingredient.

To be more specific, a conductive layer is prepared on an insulating layer of a PWB, and the conductive layer other than the mounting lands for inserted parts and surface-mounting parts is covered with solder resist. Then a film made of the foregoing material is formed on the solder resist. The present invention provides thus formed PWBs.

The present invention can also provide the components, coated with the film made from the material, such as capacitors, semiconductors, heat sinks and the like which need to be soldered.

Exemplary Embodiment 1

Exemplary embodiments of the present invention are demonstrated hereinafter with reference to the accompanying drawings. First, an electronics component is demonstrated.

Figure 2:
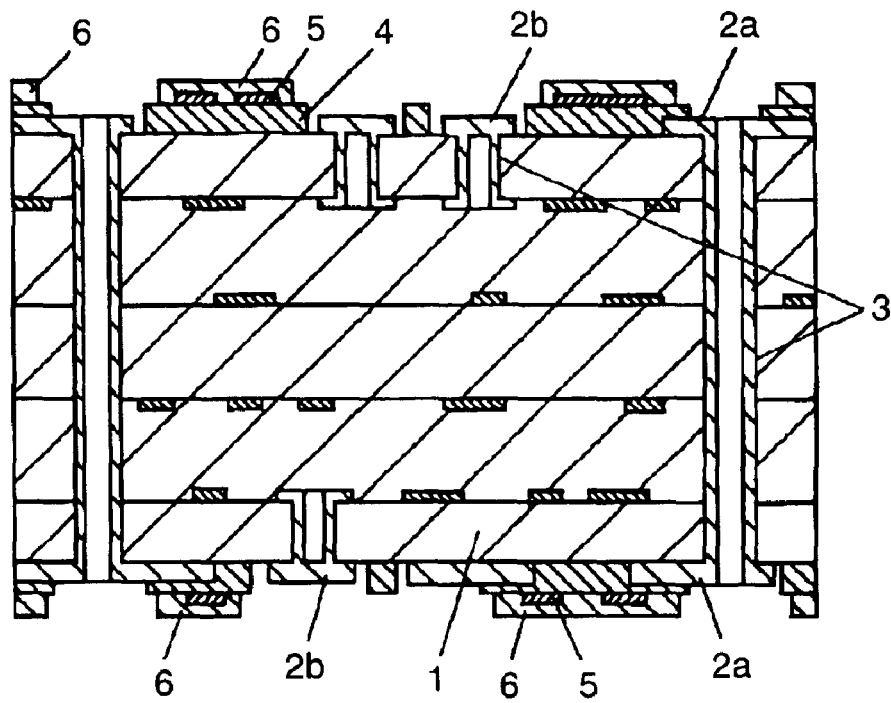
FIG. 2 is a sectional view of a multilayer PWB in accordance with the first exemplary embodiment of the present invention.

FIG. 1 is a sectional view of an essential part of copper through-hole printed wiring board (PWB), and FIG. 2 is a sectional view of an essential part of multilayer PWB. The PWBs shown in FIG. 1 and FIG. 2 comprise the following elements:

insulated substrate 1 (grade FR-4, CEM-3);

conductive layer 2a;

land 2b to be used for soldering;

through-hole 3 for connecting conductive layers on both the faces;

solder resist 4;

road map (parts layout) 5; and overcoat layer 6 formed by curing electronics-component material including repellent.

Ultraviolet curing ink is used as the electronics-component material considering the productivity of the PWBs.

The electronics-component material includes the following major ingredients:

curable resin in a given quantity as base resin, such as bisphenol A-type epoxy acrylate-base resin (BEA), or phenol novolac type epoxy acrylate-base resin (PEA);

filler in a given quantity such as silica or talc;

reactive diluent such as acrylic monomer;

ink component of additive (photo-initiator, thixotropic modified agent, cooper foil adhesion increasing agent); and deltamethrin 45 in a given quantity as repellent of vapor pressure 2000 nPa.

Deltamethrin is selected from Table 1 below that lists pyrethroid-base or pyrethroid-like repellents, the selected one should satisfy a vapor pressure of less than 10,000 nPa at room temperature (20–30° C.).

TABLE 1

List of Repellent
◎ Agents of pyrethroid-base or pyrethroid-like-base

| Agent | Standing status | Molecular weight | Melting point (° C.) | Vapor Pressure (nPa) |
|---|---|---|---|---|
| acrinathrin | Colorless crystal | 541.4 | 81.5–82 | 390 |
| bifenthrin | Crystal | 422.9 | 68–70.6 | 24,000 |

TABLE 1-continued

List of Repellent
ⓒ Agents of pyrethroid-base or pyrethroid-like-base

| Agent | Standing status | Molecular weight | Melting point (° C.) | Vapor Pressure (nPa) |
|---|---|---|---|---|
| cycloprothrin | Viscous liquid | 482.4 | — | 2,130 |
| β-cyfluthrin | Yellowish oil | 434.3 | cis-form 81/ trans-form 106 | cis-form 10/ trans-form 90 |
| λ-cyhalothrin | Colorless solid | 449.9 | — | 200 |
| cypermethrin | White crystal powder | 416.3 | 83.2 | 230 |
| cyphenothrin | Yellowish brown oil | 375.5 | — | 400,000 |
| deltamethrin | Colorless crystal powder | 505.2 | 98–101 | 2,000 |
| fenvalerate | Yellowish oil liquid | 419.9 | — | 37,000 |
| flucythrinate | Liquid | 451.4 | — | 1,200 |
| τ-fulvalinate | Yellowish viscous liquid | 502.9 | — | 13,000 |
| permethrin | Yellowish brown oil | 391.3 | 34–39 | 45,000 |
| phenothrin | yellow-brown liquid | 350.5 | — | 160,000 |
| resmethrin | white wax solid | 338.5 | 43–48 | 1,500 |
| kadethrin | Yellowish brown oil | 396.5 | 31 | 100,000 |
| silafluofen | Colorless odorless liquid | 408.6 | — | 731,500 |
| tefluthrin | Colorless solid | 418.7 | 44.6 | 80,000,000 |
| d-tetramethrin | Yellowish solid | 331.4 | 40–60 | 320,000 |
| tralomethrin | Pink-yellow resinous solid | 665.0 | 138–148 | 0.017 |

A use of epoxy acrylate-base resin as curable resin (base resin) increases bonding strength with other curable resin film such as photo solder-resist or thermosetting film.

The foregoing two kinds of PWBs are mounted with electronics components such as semiconductors, capacitors, and resistors. The PWBs undergo mounting processes including the solder-flow mounting, solder-reflow mounting or a combination of both of them, so that the stuffed PWB is completed, and the PWB is installed in the housing of an electronics apparatus before the apparatus is provided.

Exemplary Embodiment 2

Electronics-component material is demonstrated hereinafter. The method of evaluating the biological assay of the material including repellent is in conformance with the test method specified by Incorporated Foundation of Japan Environmental Health Center. The test method uses a repelling rate (repellent effect) of cockroach, and this rate is used in this embodiment.

Here is the test method:

(1) evaluation of cockroach repelling rate German cockroach is put in a vat made from resin, of which dimensions are W 30×D 20×H 20 cm. Food and water are placed at the center, and appropriate light is given.

(2) On both sides of the vat, a shelter made of the PWB of the present invention and another shelter made of a conventional PWB are provided for evaluation.

(2)-1 The PWB of the present invention comprises the following elements:
an insulated substrate of 8×8 cm;
solder-resist formed across the insulated substrate; and
film made from the electronics-component material including repellent, the film being formed on the solder-resist and having holes of 1.13 mm diameter, 25±20 μm thickness and provided at 2 mm pitches.

(2)-2 The conventional PWB as a comparison specimen comprises the following elements:
an insulated substrate of 8×8 cm; and
solder-resist formed across the insulated substrate.
No material including repellent are provided at all.

Figure 3:
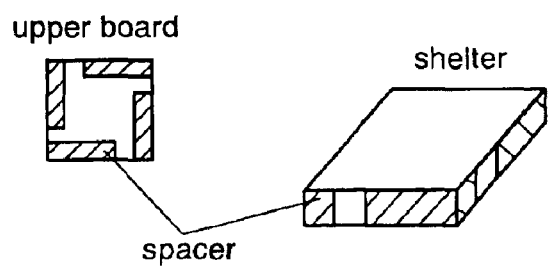
FIG. 3 is a schematic diagram illustrating a method of biological assaying used in an exemplary embodiment of the present invention.
Figure 3:
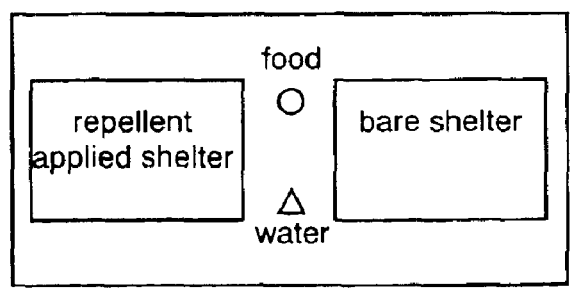

(2)-3 The shelter is formed of a lower board (thickness 0.8 mm), an upper board (thickness 0.8 mm), and a spacer. The PWB of the present invention and the conventional PWB are used as the lower board. The upper board is formed of, e.g., plywood, or others common to both the shelters, and a spacer (thickness 4.5–5 mm) is prepared for making a space (height approx. 4.8 mm) so that the cockroach tends to build a nest. Place the spacers at four corners on the lower board and put the upper board on the spacers, thereby completing the shelter (refer to FIG. 3).

(3) In 24 hours, count the number of German cockroaches that build nests in the respective shelters and the number of German cockroaches outside the shelters, for calculating the repelling rate.

Repelling rate (%)=100×{1−the number of cockroaches in the agent-applied shelter/(cockroaches in the bare shelter+cockroaches outside the shelters)}

(4) The test is repeated three times considering the dispersion due to light, difference in temperature and humidity, and individual differences. The repelling rate is calculated using the total numbers. The cockroach is also attracted by heat, and this must be evaluated; however, for the purpose of making simple and quantitative evaluation, instinct of building nest in a shelter is mainly evaluated here.

This second embodiment refers to the vapor pressure of the repellent and the repelling rate after the PWB undergoes the reflow mounting process. The electronics-component material used in the second embodiment and onward embodiments has an appropriate composition of ingredients and includes repellent considering the physical property and manufacturing conditions of PWBs. The appropriate composition means that the PWB satisfies given criteria of the general properties, i.e., pencil hardness, adhesion test (tape test), chemical resistance, solvent resistance, and insulating characteristics. Further, printability and curability in applying repellent to the PWB are taken into consideration. The details of those test results are omitted here.

Electronics-component material A to be tested is ultraviolet curing ink that includes the following ingredients:
BEA and PEA totaled: 100 parts by weight;
Silica and talc as filler totaled: 50 parts by weight;
Acrylic monomer as reactive diluent: 15 parts by weight;
Additive (photo-initiator, thixotropic modified agent, copper foil adhesion increasing agent): 15 parts by weight; and
Acrinathrin of 390 nPa vapor pressure as repellent: 35 parts by weight.

Other electronics-component materials (1)–(9), actually ultraviolet curing inks, are also tested. They have similar ingredients to material A discussed above except the repellent. They include the following repellents instead of the acrinathrin. Material (1): cycloprothrin (vapor pressure 2130 nPa), Material (2): λ-cyhalothrin (200 nPa), Material (3): cypermethrin (230 nPa), Material (4): cyphenothrin (400,000 nPa), Material (5): deltamethrin (2,000 nPa), Material (6): fenvalerate (37,000 nPa), Material (7): flucythrinate (1,200 nPa), Material (8): permethrin (45,000 nPa), and Material (9): kadethrin (100,000 nPa).

Test samples are prepared using the foregoing ten kinds of the materials, namely, ultraviolet curing inks including the foregoing ten kinds of repellents. Those inks are printed on PWBs in dot pattern of 25 μm thickness, and cured with ultraviolet ray of 10 kJ/m², so that film is formed.

Figure 4:
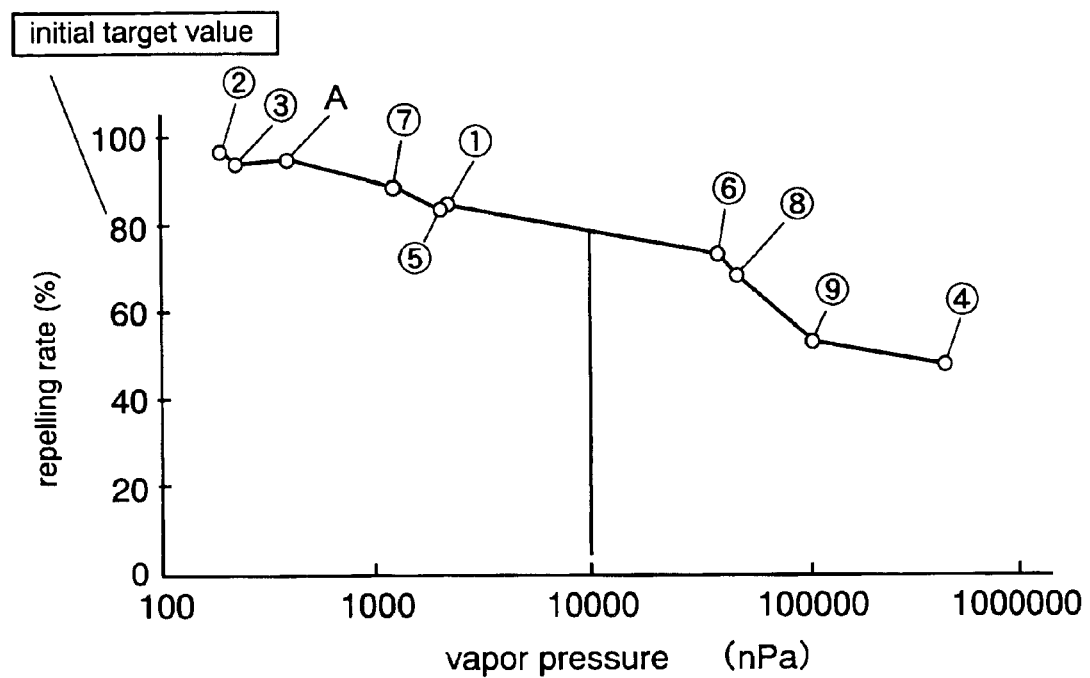
FIG. 4 shows relations between electronics-component material and repelling rates in accordance with a second exemplary embodiment of the present invention.

Those PWBs undergo solder-reflow mounting process twice. The reflow process needs 210 seconds to raise the temperature from 200° C. to the peak temperature of 250° C. on the PWB surface. Then the shelters to be used in biological assay are built with those PWBs. FIG. 4 shows the assay result (initial status before the durability is tested). FIG. 4 tells that the following five samples satisfy a target initial repelling rate of 80%: Material (1): cycloprothrin (vapor pressure 2,130 nPa), Material (2): λ-cyhalothrin (200 nPa), Material (3): cypermethrin (230 nPa), Material (5): deltamethrin (2,000 nPa), and Material (7): flucythrinate (1,200 nPa). Those five materials have the vapor pressure of less than 10,000 nPa.

The reason why the target initial repelling rate is set at 80% is this: In the repellent industry including the manufacturers thereof, it is said that the initial repelling rate must be not less than 60%. However, since the present invention is applied to electronics apparatuses, a target is set at the higher rate. This target rate of 80% has been proved by the data: Single-sided PWBs using the material that includes conventional repellent were built-in electronics apparatuses. The PWBs underwent solder-flow mounting process and their initial repelling rate is not less than 80%. The apparatuses have not experienced being damaged or built nests by vermin for these several years.

Exemplary Embodiment 3

Electronics-component materials include a different repellent, and each agent differs in content and vapor pressure. The ingredients of the materials are in appropriate composition considering physical property and manufacturing condition of the PWBs. The third embodiment refers to a repelling rate of the PWBs manufactured and undergone the reflow-mounting process.

Electronics-component material (1) includes a conventional repellent, namely, material (1) is ultraviolet curing ink that comprises the following elements:

BEA as base resin: 100 parts by weight;

Silica and talc as filler: 70 parts by weight;

Acrylic monomer as reactive diluent: 30 parts by weight;

Additive (photo-initiator, thixotropic modified agent, copper foil adhesion increasing agent): 5 parts by weight; and Permethrin of 45,000 nPa vapor pressure as repellent: 130 parts by weight.

Material (2) is ultraviolet curing ink for comparison purpose and comprises the following elements:

BEA and PEA as base resin totaled: 100 parts by weight;

Silica and talc as filler totaled: 50 parts by weight;

Acrylic monomer as reactive diluent: 15 parts by weight;

Additive (photo-initiator, thixotropic modified agent, copper foil adhesion increasing agent): 15 parts by weight; and Permethrin of 45,000 nPa vapor pressure as repellent: 35 parts by weight.

Material (2) is in appropriate composition to be used for PWBs.

Material (3) is ultraviolet curing ink of the present invention and comprises the following elements:

BEA and PEA as base resin totaled: 100 parts by weight;

Silica and talc as filler totaled: 70 parts by weight;

Acrylic monomer as reactive diluent: 140 parts by weight;

Additive (photo-initiator, thixotropic modified agent, copper foil adhesion increasing agent): 35 parts by weight; and Deltamethrin of 2,000 nPa vapor pressure as repellent: 45 parts by weight.

Material (3) is in appropriate composition to be used for PWBs, and selects the repellent of rather lower vapor pressure.

Test samples are prepared using the foregoing three kinds of the materials, namely, ultraviolet curing inks. Those inks are printed on PWBs in dot pattern of 25 μm thickness, and cured with ultraviolet ray of 10 kJ/m², so that film is formed. Some of those PWBs undergo solder-flow mounting process once, where the peak temperature of the PWB surface is 250° C. Another some of the PWBs undergo solder-reflow process once or twice, the process needs 180 seconds before the temperature of the PWB surface rises to the peak temperature of 240° C. from 200° C.

Figure 5:
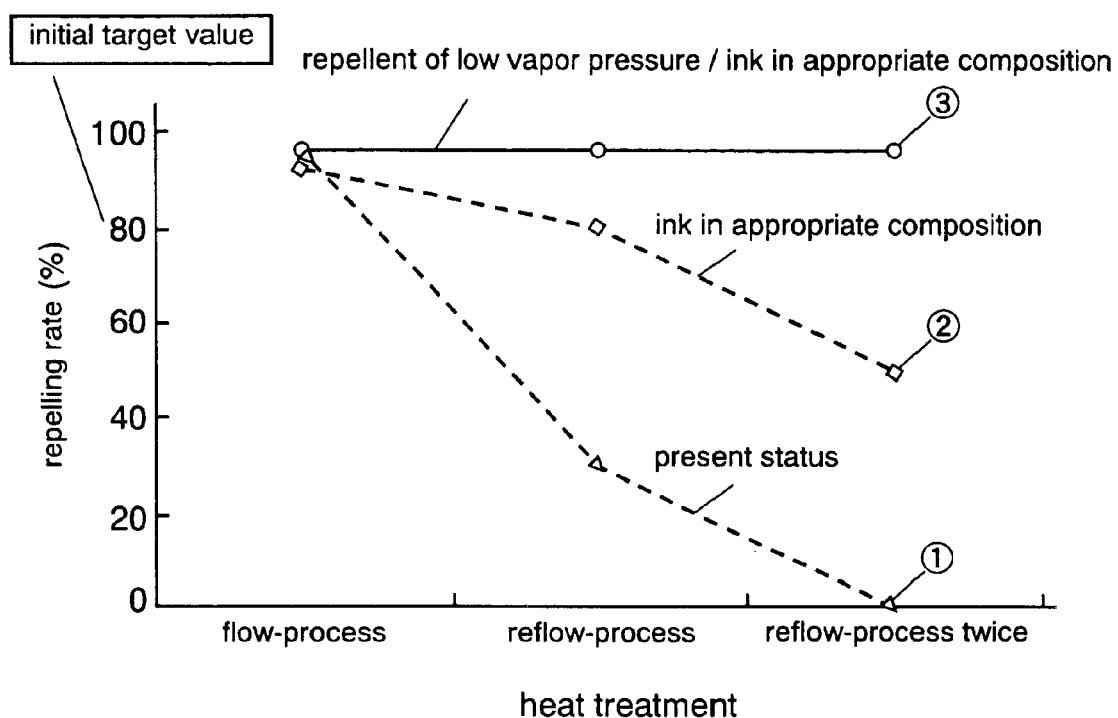
FIG. 5 shows relations between electronics-component material and repelling rates in accordance with a third exemplary embodiment of the present invention.

Shelters for biological assay are built using those test samples. FIG. 5 shows the assay result (an initial status before durability is tested.) FIG. 5 tells that material (1) undergone the solder-reflow process once does not satisfy the target initial repelling rate of 80%.

Material (2) undergone the solder-reflow process once satisfies the target rate of 80%; however material (2) undergone the reflow process twice cannot satisfy the target rate.

Material (3) that includes the repellent, of which vapor pressure is less than 10,000 nPa, undergone the reflow process twice satisfies the target rate of 80%.

Exemplary Embodiment 4

Electronics-component materials include a repellent of which vapor pressure is less than 10,000 nPa, in different content by amount. The ingredients of respective materials are in appropriate composition considering physical property and manufacturing condition of the PWBs. The fourth embodiment refers to a repelling rate of the PWBs manufactured and undergone the reflow-mounting process.

Electronics-component material A to be tested is ultraviolet curing ink that comprises the following elements:

BEA and PEA as base resin totaled: 100 parts by weight;

Silica and talc as filler totaled: 50 parts by weight;

Acrylic monomer as reactive diluent: 100 parts by weight;

Additive (photo-initiator, thixotropic modified agent, copper foil adhesion increasing agent): 20 parts by weight; and Deltamethrin of 2,000 nPa vapor pressure as repellent: 5 parts by weight.

Material A is in appropriate composition to be used for PWBs.

Other sample materials (1)–(7) to be tested are the ultraviolet curing inks of which content by amount of repellent are changed as follows:

Material (1): 10 parts by weight, Material (2): 15 parts by weight, Material (3): 20 parts by weight, Material (4): 25 parts by weight, Material (5): 30 parts by weight, Material (6): 35 parts by weight, and Material (7): 40 parts by weight.

Figure 6:
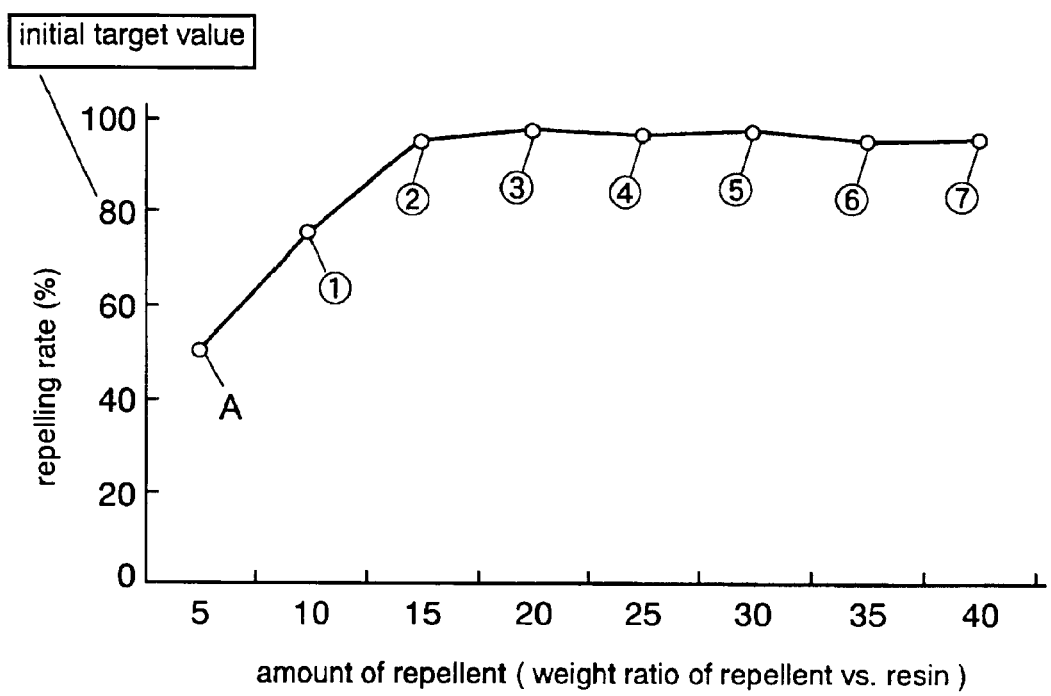
FIG. 6 shows relations between electronics-component material and repelling rates in accordance with a fourth exemplary embodiment of the present invention.

Test samples are prepared using the foregoing eight kinds of the materials, namely, ultraviolet curing inks. Those inks are printed on PWBs in dot pattern of 30 µm thickness, and cured with ultraviolet ray of 10 kJ/m², so that film is formed. Those PWBs undergo solder-reflow process twice, the process needs 210 seconds before the temperature of the PWB surface rises to the peak temperature of 260° C. from 200° C. Shelters for biological assay are built using those test samples. FIG. 6 shows the assay result (an initial status before durability is tested.)

FIG. 6 tells that the amount of repellent that satisfies the target initial repelling rate of 80% ranges from 15 to 40 parts by weight.

Exemplary Embodiment 5

Electronics-component materials include a repellent of which vapor pressure is less than 10,000 nPa. The materials include silica and talc in different additive ratio in order to determine a proper composition of the material to be used for PWBs considering the physical property and manufacturing condition of the PWBs. The fifth embodiment refers to a repelling rate of the PWBs manufactured and undergone the reflow-mounting process.

Electronics-component material A to be tested is ultraviolet curing ink that comprises the following elements:

BEA and PEA as base resin totaled: 100 parts by weight;

Silica as filler: 100 parts by weight; (additive ratio of silica/talc=100/0)

Acrylic monomer as reactive diluent: 100 parts by weight;

Additive (photo-initiator, thixotropic modified agent, copper foil adhesion increasing agent): 20 parts by weight; and Deltamethrin of 2,000 nPa vapor pressure as repellent: 25 parts by weight.

Material A is in appropriate composition to be used for PWBs.

Other materials (1)–(5) to be tested include silica and talc in different additive ratios: Material (1) includes silica/talc at the ratio of 90/10 parts by weight. Material (2): 80/20, Material (3): 70/30, Material (4): 60/40, and Material (5): 50/50.

Figure 7:
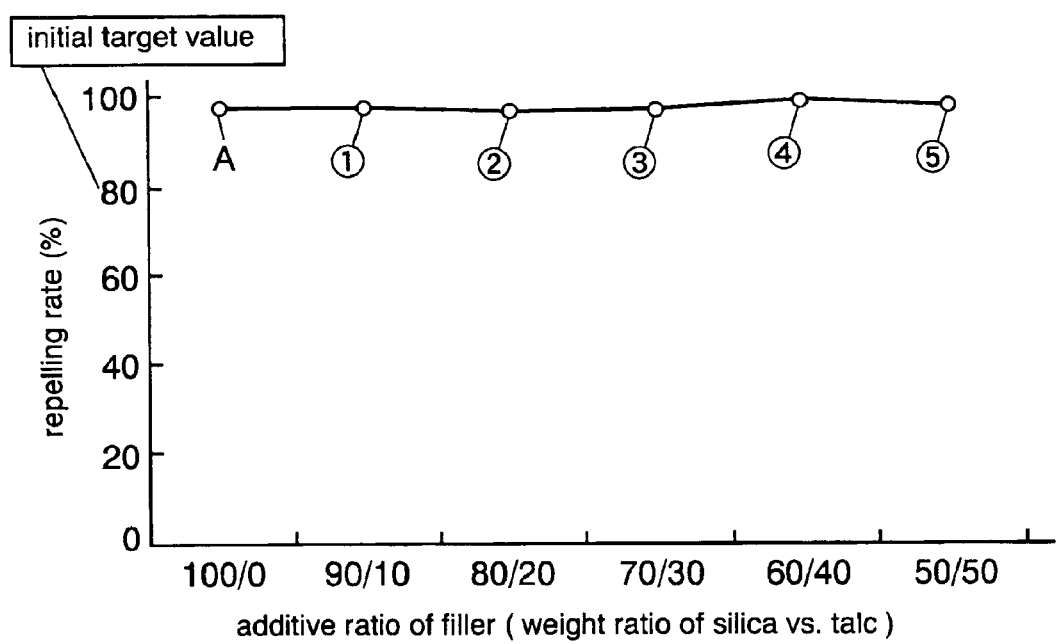
FIG. 7 shows relations between electronics-component material and repelling rates in accordance with a fifth exemplary embodiment of the present invention.

Test samples are prepared using the foregoing six kinds of the materials, namely, ultraviolet curing inks. Those inks are printed on PWBs in dot pattern of 30 µm thickness, and cured with ultraviolet ray of 10 kJ/m², so that film is formed. Those PWBs undergo solder-reflow process twice, the process needs 210 seconds before the temperature of the PWB surface rises to the peak temperature of 260° C. from 200° C. Shelters for biological assay are built using those test samples. FIG. 7 shows the assay result (an initial status before durability is tested.) FIG. 7 tells that the weight ratios of silica vs. talc ranging from 100/0 to 50/50 satisfy the target initial repelling rate of 80%, and addition of another filler to silica does not so much influence the repelling rate.

The test discussed above proves that the weight ratio of silica vs. talc can be set arbitrarily within the foregoing range, and this weight ratio does not lower the repelling rate. As a result, the optimum material for PWBs can be selected satisfying physical and mechanical properties such as adherence, heat resistance of the PWB, and in-use environment as well as manufacturing condition of the PWB.

Exemplary Embodiment 6

Electronics-component materials include a repellent of which vapor pressure is less than 10,000 nPa. The materials include PEA and BEA in different weight ratio in order to determine a proper composition of the material to be used for PWBs considering the physical property and manufacturing condition of the PWBs. The sixth embodiment refers to a repelling rate of the PWBs manufactured and undergone the reflow-mounting process.

Electronics-component material A to be tested is ultraviolet curing ink that comprises the following elements:

PEA as base resin: 100 parts by weight (weight ratio of PEA vs. BEA=100/0);

Silica and talc as filler totaled: 70 parts by weight;

Acrylic monomer as reactive diluent: 140 parts by weight;

Additive (photo-initiator, thixotropic modified agent, copper foil adhesion increasing agent): 35 parts by weight; and Deltamethrin of 2,000 nPa vapor pressure as repellent: 45 parts by weight.

Material A is in appropriate composition to be used for PWBs.

Other materials (1)–(4) to be tested include PEA and BEA at the following weight ratios: Material (1): weight ratio of PEA vs. BEA=75/25, Material (2): 50/50, Material (3): 25/75, and Material (4): 0/100.

Figure 8:
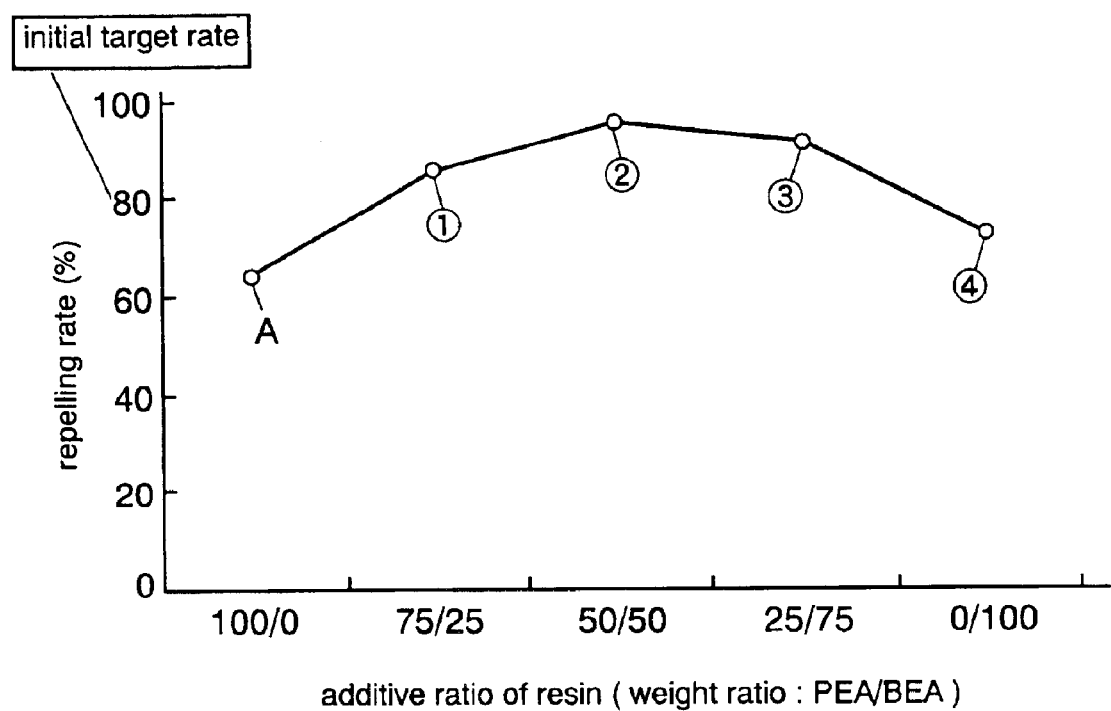
FIG. 8 shows relations between electronics-component material and repelling rates in accordance with a sixth exemplary embodiment of the present invention.

Test samples are prepared using the foregoing five kinds of the materials, namely, ultraviolet curing inks. Those inks are printed on PWBs in dot pattern of 30 µm thickness, and cured with ultraviolet ray of 10 kJ/m², so that film is formed. Those PWBs undergo solder-reflow process twice, the process needs 210 seconds before the temperature of the PWB surface rises to the peak temperature of 260° C. from 200° C. Shelters for biological assay are built using those test samples. FIG. 8 shows the assay result (an initial status before durability is tested.) FIG. 8 tells that the weight ratios ranging from 75/25 to 25/75 satisfy the target initial repelling rate of 80%.

The foregoing test proves that the weight ratio of PEA vs. BEA can be set arbitrarily within the foregoing range, and this weight ratio does not lower the repelling rate. As a result, the optimum material for PWBs can be selected satisfying physical and mechanical properties such as adherence, heat resistance of the PWB, and in-use environment as well as manufacturing condition of the PWB.

INDUSTRIAL APPLICABILITY

Electronics-component material is provided. The material does not lower repelling effect even under severe soldering conditions. A use of this material in electronics components including printed wiring boards restraints vermin, such as cockroaches or ants that have sensory nerve, from invading electronics apparatuses, thereby preventing the apparatuses from failures due to carcasses and droppings of the vermin.

What is claimed is:

1. Material of electronics components that need a soldering process, the material comprising:

curable resin including mixture of phenol novolac-type epoxy acrylate resin and bisphenol A-type epoxy acrylate resin;

filler; and repellent of which vapor pressure is less than 10,000 nPa, wherein the repellent is one of pyrethroid-base neurotransmitting agent and pyrethroid-like-based neurotransmitting agent; and wherein the repellent is at least one agent selected from the group consisting of acrinathrin, cycloprothrin, λ-cyhalothrin, cypermethrin, deltamethrin, and flucythrinate.

2. The material of claim 1, wherein the soldering process carries out solder-reflow mounting at least once.

3. The material of claim 1, wherein the soldering process uses lead-free solder.

4. The material of claim 1, wherein the filler includes at least one of silica and talc.

5. The material of claim 4, wherein a weight ration of the silica vs. the talc in mixture ranges from 100/0 the 50/50.

6. The material of claim 1, wherein a weight ration of the phenol novolac-type epoxy acrylate resin vs. bisphenol A-type epoxy acrylate resin in the mixture as the curable resin ranges from 75/25 to 25/75.

7. The material of claim 1, wherein the curable resin includes:
 phenol novolac-type epoxy acrylate resin and bisphenol A-type epoxy acrylate resin totaled 100 parts by weight;
 wherein the filler includes: silica and talc totaled 50 parts by weight, and the material further comprising: reactive diluent that includes acrylic monomer 15 parts by weight.

8. The material of claim 1, wherein the curable resin includes:
 phenol novolac-type epoxy acrylate resin and bisphenol A-type epoxy acrylate resin totaled 100 parts by weight;
 wherein the filler includes: silica and talc totaled 50 parts by weight, and the material further comprising: reactive diluent that includes acrylic monomer 100 parts by weight.

9. The electronics component of claim 1, wherein a film made from the material is formed at a given place of the electronics component.

10. The electronics component of claim 9 is a printed wiring board including a mounting land to be used for soldering.

11. The electronics component of claim 9, wherein the given place is a surface layer of a printed wiring board.

12. Material of electronics components that need a soldering process, the material comprising:
 curable resin including mixture of phenol novolac-type epoxy acrylate resin and bisphenol A-type acrylate resin;
 filler; and
 repellent of which vapor pressure is less than 10,000 nPa, wherein the repellent includes deltamethrin at least 15 parts by weight.

13. Material of electronics components that need a soldering process, the material comprising:
 curable resin including mixture of phenol novolac-type epoxy acrylate resin and bisphenol A-type epoxy acrylate resin;
 filler; and
 repellent of which vapor pressure is less than 10,000 nPa,
 wherein the curable resin includes:
 phenol novolac-type epoxy acrylate resin and bisphenol A-type epoxy acrylate resin totaled 100 parts by weight;
 wherein the repellent includes: deltamethrin 25 parts by weight, and the material further comprising: reactive diluent that includes acrylic monomer 100 parts by weight.

14. Material of electronics components that need soldering process, the material comprising:
 curable resin including mixture of phenol novolac-type epoxy acrylate resin and bisphenol A-type epoxy acrylate resin;
 filler; and
 repellent of which vapor pressure is less than 10,000 nPa,
 wherein the filler includes: silica and talc totaled 70 parts by weight,
 wherein the repellent includes: deltamethrin 45 parts by weight, and the material further comprising: reactive diluent that includes acrylic monomer 140 parts by weight.

15. The material of claim 14, wherein the curable resin includes:
 phenol novolac-type epoxy acrylate resin and bisphenol A-type epoxy acrylate resin totaled 100 parts by weight;
 wherein the filler includes: silica and talc totaled 70 parts by weight,
 wherein the repellent includes deltamethrin 45 parts by weight, and
 the material further comprising: reactive diluent that includes acrylic monomer 140 parts by weight.

* * * * *

UNITED STATES PATENT AND TRADEMARK OFFICE
CERTIFICATE OF CORRECTION

PATENT NO.   : 6,927,272 B2
DATED        : August 9, 2005
INVENTOR(S)  : Kazumi Iwasaki It is certified that error appears in the above-identified patent and that said Letters Patent is hereby corrected as shown below:

<u>Column 10,</u>
Line 59, change "base" to -- based --.

<u>Column 11,</u>
Line 5, change "ration" to -- ratio --.
Line 6, change "100/0 the" to -- 100/0 to --.
Line 7, change "ration" to -- ratio --.
Line 41, after "A-type" and -- epoxy --.

Signed and Sealed this

Twenty-first Day of March, 2006

JON W. DUDAS
*Director of the United States Patent and Trademark Office*

UNITED STATES PATENT AND TRADEMARK OFFICE
CERTIFICATE OF CORRECTION

PATENT NO.       : 6,927,272 B2                                          Page 1 of 1
APPLICATION NO.  : 10/333772
DATED            : August 9, 2005
INVENTOR(S)      : Kazumi Iwasaki It is certified that error appears in the above-identified patent and that said Letters Patent is hereby corrected as shown below:

Column 10,
Line 59, change "base" to -- based --.

Column 11,
Line 5, change "ration" to -- ratio --.
Line 6, change "100/0 the" to -- 100/0 to --.
Line 7, change "ration" to -- ratio --.
Line 41, after "A-type" add -- epoxy --.

This certificate supersedes Certificate of Correction issued March 21, 2006.

Signed and Sealed this

Twenty-seventh Day of June, 2006

JON W. DUDAS
*Director of the United States Patent and Trademark Office*